United States Patent [19]

Spies

[11] Patent Number: 4,843,320
[45] Date of Patent: Jun. 27, 1989

[54] TRANSIENT ELECTROMAGNETIC METHOD FOR DETECTING CORROSION ON CONDUCTIVE CONTAINERS

[75] Inventor: Brian R. Spies, McKinney, Tex.

[73] Assignee: Atlantic Richfield Company, Los Angeles, Calif.

[21] Appl. No.: 134,368

[22] Filed: Dec. 17, 1987

[51] Int. Cl.$^4$ .................. G01N 27/82; G01R 33/12; G01B 7/10
[52] U.S. Cl. ................................ 324/240; 324/71.2; 324/229
[58] Field of Search ................ 324/229, 230, 236–243, 324/220, 221, 65 CR, 71.1, 71.2, 336, 425

[56] References Cited

U.S. PATENT DOCUMENTS

| | | | |
|---|---|---|---|
| 3,229,197 | 1/1966 | Renken | 324/240 |
| 3,315,155 | 4/1967 | Colani | 324/239 |
| 3,532,969 | 10/1970 | McCullough et al. | 324/239 X |
| 3,707,672 | 12/1972 | Miller et al. | 324/239 |
| 3,745,452 | 7/1973 | Osburn et al. | 324/254 X |
| 4,194,149 | 3/1980 | Holt et al. | 324/238 X |
| 4,271,393 | 6/1981 | Hansen et al. | 324/240 |
| 4,418,574 | 12/1983 | Flournoy | 324/229 X |
| 4,611,170 | 9/1986 | Stanley et al. | 324/239 X |
| 4,717,006 | 1/1988 | Chapman et al. | 324/239 X |

OTHER PUBLICATIONS

Spies, "Scale Model Studies of a Transient Electromagnetic Prospecting System Using an Interactive Minicomputer", IEEE Transactions on Geoscience Electronics, vol. GE-17, No. 2, Apr. 1979.

Flora, "Deep-Penetration Eddy-Current Techniques to Detect Corrosion Under Insulation", MTI Publication No. 22, Materials Technology Institute of the Chemical Process Industries, Inc., June 1986.

Primary Examiner—Gerard R. Strecker
Attorney, Agent, or Firm—Geoffrey A. Mantooth; Arthur F. Zobal; James C. Fails

[57] ABSTRACT

There is disclosed a method for detecting corrosion on the walls of conductive containers wherein a transmitting antenna induces a current into a portion of the container wall and the decay of the induced current is detected by a receiving antenna, with a record of the decay of the induced current being created. The record is interpreted to determine the thickness of the container wall portion and the presence or absence of corrosion is inferred. One method of interpretation uses reference records from container walls having known parameters for comparison. Another method of interpretation examines the times that the induced current reaches the container wall portion surface that is farthest from the antennas.

29 Claims, 5 Drawing Sheets

TRANSIENT ELECTROMAGNETIC METHOD FOR DETECTING CORROSION ON CONDUCTIVE CONTAINERS

FIELD OF THE INVENTION

The present invention relates to a non-destructive method from detecting corrosion on electrically conductive containers such as pipelines, storage vessels, pressure vessels and the like.

BACKGROUND OF THE INVENTION

Oil and gas pipelines located at Alaska's Prudhoe Bay are wrapped with a jacket of insulating material to prevent the rapid cooling, and provide better transportability, of oil and gas fluids. The outer surface of the insulation is covered by a metal jacket for keeping out moisture. The metal jacket is typically provided in two half portions with each portion having flanges for aiding in the retention of the jacket on the pipeline. The two half portions of the jacket are joined together at the flanges which form seams. Water occasionally enters through the jacket seams and travels through the insulation to the pipe where it causes corrosion.

Prior art methods of detecting pipeline corrosion have proven inadequate. For example, pigs with corrosion detection equipment can only be used on pipelines that have access locations; many pipelines lack such locations. Ultrasonic detection methods require removal of the metal jacket and insulation, a timely and expensive procedure. Radiography detection methods are potentially hazardous and the equipment is cumbersome, requiring impractical or inconvenient adjacent vehicular support. Furthermore, with radiography methods its is often difficult to distinguish between corrosion pits filled with corrosion products and uncorroded portions of pipe walls. What is needed then is a method of detecting corrosion through insulation and the surrounding jacket, and which method can be practiced with portable equipment.

Electromagnetic probing techniques provide such a method for detecting corrosion through insulation. In the prior art, frequency domain electromagnetic probing techniques are used to detect corrosion in aircraft fuel tanks. Frequency domain electromagnetic probing techniques utilize a small number of frequencies and measure magnitude and phase differentials between the transmitted signals and the received signals. However, because frequency domain techniques, as a practical matter, utilize only a small number of frequencies, the amount of information obtained is inherently limited, thus detracting from the accuracy of the techniques.

It is an object of the present invention to provide a method for detecting corrosion on insulated conductive containers, wherein said method has improved accuracy in detection and can detect corrosion through insulation.

DESCRIPTION OF THE PREFERRED EMBODIMENT

Figure 1:
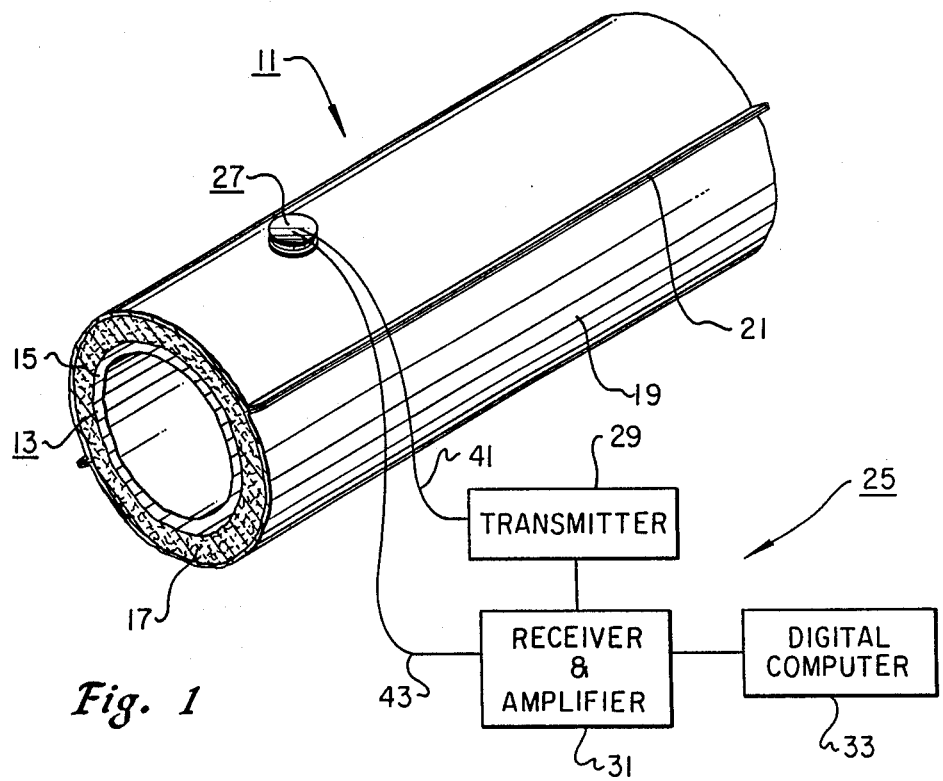
FIG. 1 is a schematic diagram showing a typical situation in whicht the method for detecting corrosion in a container in accordance with a preferred embodiment of the present invention can be practiced, together with typical testing apparatus.
Figure 2:
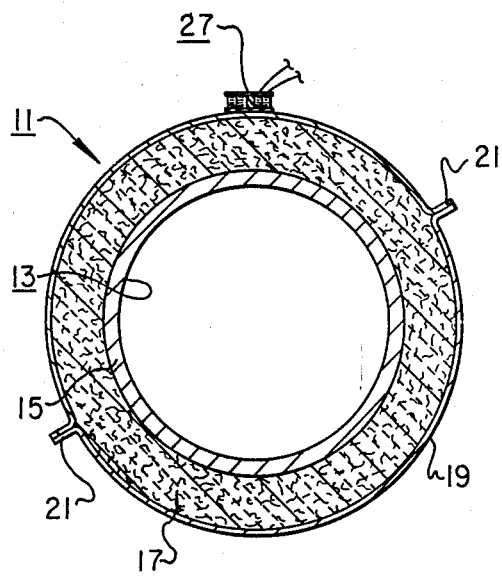
FIG. 2 is a schematic diagram showing a transverse cross-section of the pipeline of FIG. 1.
Figure 3:
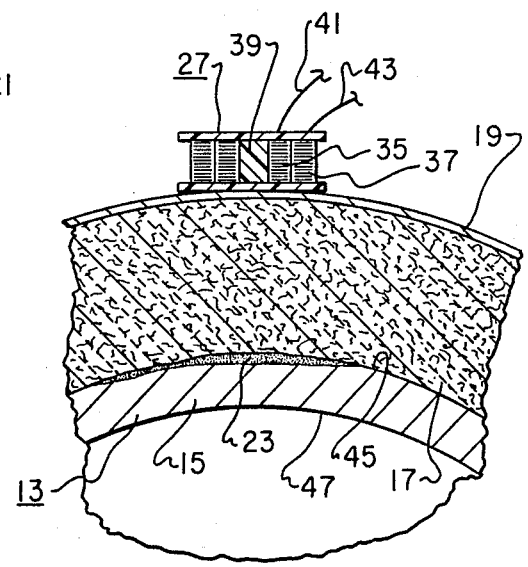
FIG. 3 is a schematic cross-sectional view showing the antenna means of FIG. 2 in detail.

In FIGS. 1-3 there is schematically shown a typical situation in which the method of detecting corrosion in electrically conductive containers 11 can be practiced, together with typical detecting apparatus 25. The method of the present invention utilizes transient electromagnetic probing (TEMP) to detect corrosion.

The conductive container shown in FIGS. 1-3 is a portion of a pipeline 11, which is of course made up of a plurality of individual pipes 13. The pipes 13 have a diameter and the pipe walls 15 have a thickness. The pipe walls 15 are made up of an electrically conductive material such as steel.

In Alaska's Prudhoe Bay region, pipelines wrapped with insulating material 17 are used to transport oil and gas fluids. The insulation 17 is provided to prevent rapid cooling of the oil and gas fluids in the pipeline and thus provide better transportability of these fluids in the pipeline. In refineries, pipelines and vessels are commonly wrapped with insulation as a safety measure in protecting personnel from high temperatures. The insulation 17 on pipelines is typically a thermoplastic foam such as polystyrene, and has a radial thickness. Surrounding the insulation 17 is a metal jacket 19 which is provided to keep out moisture. The jacket 19 has a thickness which is much less than the thickness of the pipe wall. The metal jacket 19 has two half portions that extend longitudinally along the pipeline. Each jacket half portion has seam means in the form of flanges 21 that extend radially outward. When the jacket half portions are assembled onto the pipeline, the respective flanges 21 abut one another to form seams. The half portions are retained in place on a pipeline by securing the respective flanges together with suitable means.

In FIG. 3, the pipe wall 15 is shown to have a corrosion pit 23 adjacent to the insulation. The corrosion acts to reduce the thickness of the pipe wall, wherein it forms the pit and fills the pit with corrosion products. The corrosion that has pitted the pipe wall is caused by water that has entered the insulation between the jacket flanges 21.

Detecting apparatus 25 is provided near that portion of the pipe wall which is to be tested for corrosion and includes antenna means 27, a transmitter 29, a receiver and amplifier 31, and a digital computer 33.

The antenna means 27 include a transmitting antenna coil 35, a receiving antenna coil 37 and core means 39. In the preferred embodiment, the transmitting and receiving antenna coils 35, 37 are wound onto the same core means 39, an arrangement which is hereinafter referred to as coincident (see FIG. 3). The core means 39, which is in the shape of a spool, is made of a non-magnetic and non-conductive material such as plastic. The number of turns of the transmitting antenna coil are kept to a minimum to minimize the inductance of the transmitting antenna and to provide for an abrupt switching off of the transmitting antenna coil. In the preferred embodiment, the transmitting antenna coil 35 is made up of 120 turns of 20 to 24 gauge wire. The receiving antenna coil 37 is made up of 400 turns of 34 to 40 gauge wire. The transmitting and receiving antenna coils 35, 37 are connected to the transmitter 29 and receiver 31 by respective pairs of wires 41, 43.

The transmitter 29 which is conventional, generates a train of pulses having magnitudes of 1 to 5 amps. As discussed in more detail below, a plurality of pulses are transmitted for each location of the antenna means 27 for data enhancement purposes. The pulses have abrupt fall times on the order of 10 to 100 microseconds. The pulses of the transmitter pulse train alternate polarity to eliminate dc bias in the instrumentation. The duration of each pulse is sufficiently long to stabilize the pulse magnitude so that there are no induced currents in the pipe wall before the end of the pulse. The transmitter 29 repeats the pulses at a repetition rate that allows all of the necessary data to be obtained for each pulse. For example, a thick pipe wall requires more time to obtain data than does a thinner pipe wall because the induced current takes longer to diffuse in the thick pipe wall. Thus, the repetition rate of pulses will typically be slower for thick pipe walls than for thinner pipe walls.

The receiver and amplifier 31 is a broad band instrument with a wide (5 or 6 orders of magnitude) dynamic range. The receiver 31, which has an A/D converter, samples the signal at a constant rate and integrates the signal over a time window or channel. The duration of the time windows increases with time. The transmitter 29 and the receiver and amplifier 31 are conventional. In practice it has been found that the SIROTEM transmitter, receiver and amplifier unit manufactured by Geoex Pty. Ltd. of Adelaide, Australia, works well. The battery operated SIROTEM unit is portable, a characteristic which allows ease of use when surveying pipelines in the field.

The digital computer 33 is a conventional portable computer with sufficient memory capacity to record the data.

The method of detecting corrosion on a conductive container of the present invention will now be described. As mentioned earlier, the method of the present invention utilizes transient electromagnetic probing (TEMP). TEMP allows the remote probing of a conductor by inducing a current into the conductor and then analyzing the decay of the current.

First, the antenna means 27 is placed on the jacket 19 so as to be in proximity with the near surface 45 of the portion of the pipeline 11 that is to be investigated. Suitable means (not shown) are used to secure the antenna means 27 in position so as to minimize any motion of the antenna means over the investigated pipe wall portion. The transmitting antenna coil 35 is then energized by the transmitter 29 with a pulse. As described above, the transmitting antenna coil 35 is energized for a sufficient period of time to stabilize the pulse magnitude, thereby insuring no eddy currents are induced into the pipeline 11. Then, the transmitting coil 35 is abruptly de-energized by the transmitter by having the pulse fall off rapidly to zero magnitude. This abrupt de-energization of the transmitting antenna coil 35 induces eddy currents into the conductors located near the coil; namely the jacket 19 and the pipe wall 15. The eddy currents, which decay and diffuse away from the antenna means 27 inside of the respective conductors, create a magnetic field that is detected as a time-varying voltage in the receiving antenna coil 37. As soon as the transmitting antenna coil is de-energized, the receiver 31 is then switched on. The receiving antenna coil 37 detects the presence of and the decay of the induced eddy currents in the conductors. The eddy currents are gradually dissipated within the conductors by resistive heat losses. The rate of diffusion is dependent on the conductivity and thickness of the conductor. The receiver 31 samples the signal as detected by the receiving antenna coil 37, whereupon it is amplified to a suitable level and sent to the digital computer 33 for storage and processing. The receiver 31 measures the signal from the time the eddy currents are first induced into the conductors until the signal becomes indistinguishable from noise. The level of noise is reduced by minimizing any motion of the receiving antenna coil 37 relative to the conductors. The received signal is unprocessed data and forms a record in the computer 33 of the decay of the induced currents in the conductors. The transmitting and receiving procedure is repeated many times with the antenna means 27 in the same location to increase the signal-to-noise ratio.

Figure 4:
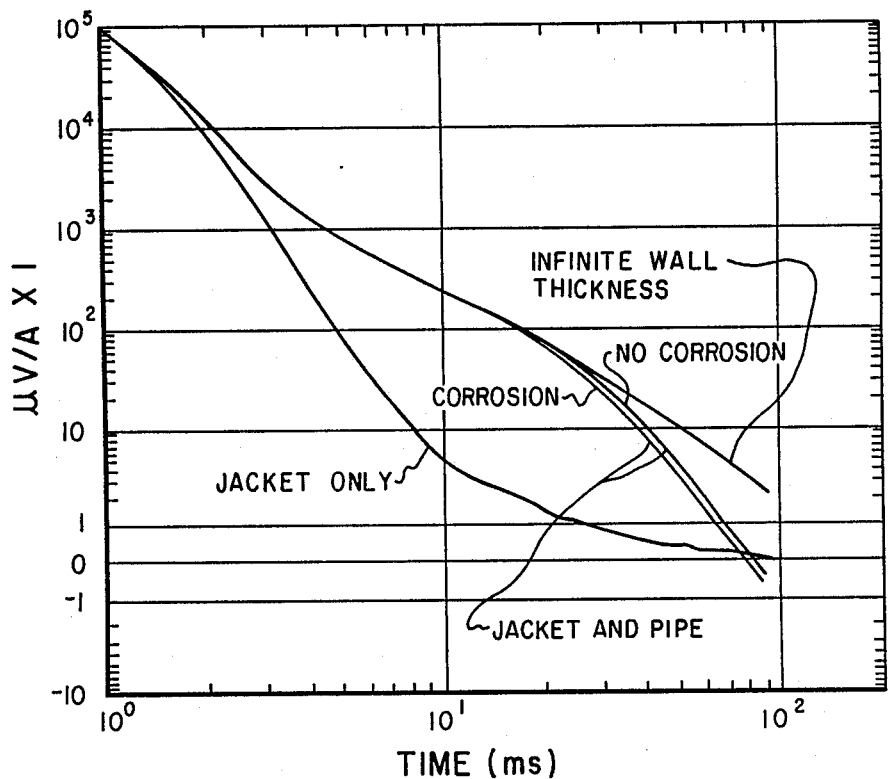
FIG. 4 is a graph showing the time domain response curves of various conductors, obtained by the transient electromagnetic probing (TEMP) method of the present invention.

The data is then processed by computer data processing means into a suitable format for interpretation. The first steps in the processing of the data involve the normalization of the received signals and the summing and averaging of the received signals. Because the transmitter 29 in the preferred embodiment is battery operated, the magnitude of the transmitter current is subjected to variation. The effects of variation in magnitude in the data are removed by normalizing the received voltage to the transmitted current. The summing and averaging of the received signals for a particular antenna means location serves to increase the signal-to-noise ratio. In particularly noisy environments, as an alternative to summing and averaging, selective stacking can be used to eliminate noisy transients. The result of this initial data processing is a time-varying response curve such as shown in FIG. 4. (FIG. 4 illustrates response curves for various conductors.)

The response curves may be interpreted in accordance with methods which will now be described, with reference to FIGS. 4–8d. Referring in particular to FIG. 4, the presence or absence of corrosion on a conductor wall is inferred by examining the shape of the various response curves which have been taken over the area of interest. The shape of each response curve depends in part on the thickness of the conductor wall.

For example, the magnitude of the response curve of an infinitely thick conductor wall decays at a fairly even rate (on a log-log graph), resulting in a fairly straight response curve, whereas the response curve of a conductor having a finite wall thickness begins to break at some point into a more pronounced downward direction that before and decays at a faster rate. This breaking phenomenon is attributed to the induced currents diffusing to and reaching the far surface 47 of the conductor wall. Response curves for thin conductor walls break at earlier times than do response curves for thicker conductor walls.

Because corrosion reduces the thickness of a conductor wall, the presence or absence of corrosion can be inferred by comparing the shape of the response curve for the investigated pipe wall portion to the shape of the response curve for an uncorroded portion of the same type of pipe. For example, in FIG. 4, the two response curves labeled "corrosion" and "no corrosion" are taken from the same pipe. The "no corrosion" response curve is taken from an uncorroded portion of the pipe and is used as a reference, while the "corrosion" response curve is taken from a different portion of the same pipe, which different portion has a pit to simulate corrosion (with the antenna means located at the same distance from the pipe wall, for both response curves). At about 17 ms (milliseconds), the "corrosion" response curve breaks into a more pronounced downward direction and begins to decay at a faster rate than before. The "corrosion" break point occurs at an earlier time than does the "no corrosion" break point (at about 25 ms), indicating that the conductor wall represented by the "corrosion" response curve is thinner than the conductor wall represented by the "no corrosion" response curve.

Figure 5:
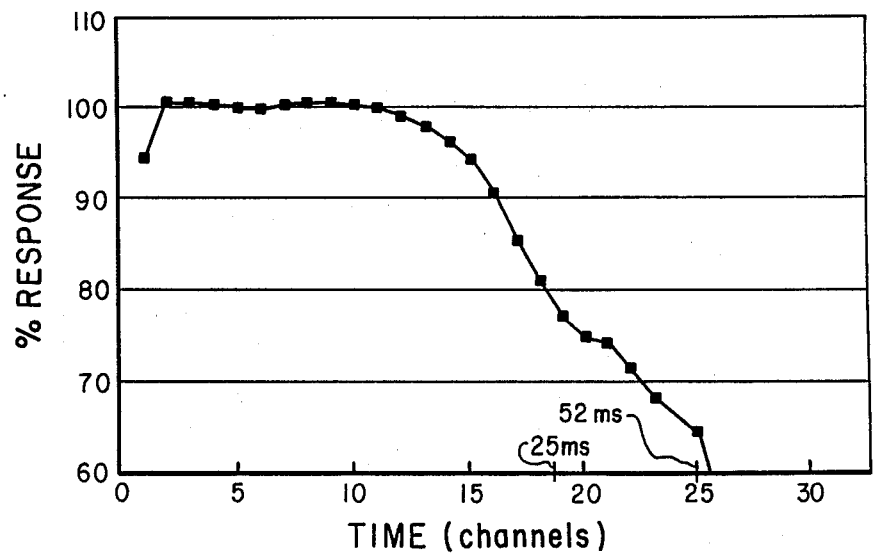
FIG. 5 is a graph of the response curve of a pit in a pipe wall, with the response curve obtained by computing the ratio of the "corrosion" to the "no corrosion" response curves of FIG. 4.

Referring now to FIG. 5, the "corrosion" and "no corrosion" response curves of FIG. 4 are compared by plotting the ratio of the two curves as a percent response curve, using the "no corrosion" response curve as a reference. The percent response curve highlights the differences between the "corrosion" and the "no corrosion" response curves. By examining the late time portions of the percent response curve (from about 17–20 ms on, which is about when the "corrosion" response curve of FIG. 4 begins to break sharply downward), one can see that the "corrosion" response curve deviates 20 to 30 percent from the "no corrosion" response curve. This 20 to 30 percent difference clearly indicates a difference in wall thickness between the corroded portion of the pipe and the uncorroded portion of the pipe.

In FIG. 4, the response curve labeled "jacket only" is that taken from the metal jacket 19, without the pipe 13. The "jacket only" response curve decays very rapidly so that by the relatively late time of 20 ms, the jacket 19 contributes very little to the total response. This is because the wall thickness of the jacket is much smaller than is the thickness of the pipe wall, so the currents diffuse much more rapidly in the jacket. Thus, for those portons of the "jacket and pipe" response curves that are of interest in locating corrosion (that is the later times), the effect of the jacket can be ignored.

Figure 7:
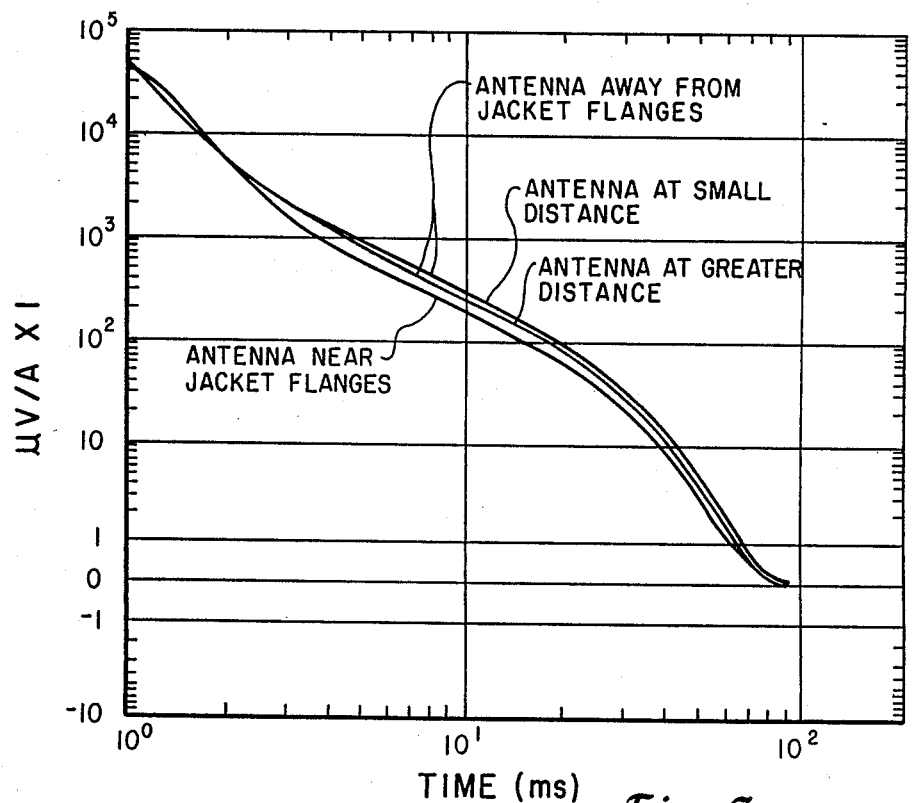
FIG. 7 is a graph showing the effects of the jacket flanges and of variations in antenna means height on time domain responses of pipe walls.

Responses measured near jacket flanges are affected quite strongly by the jacket flanges at all times, as shown in FIG. 7. A response measured near jacket flanges can be corrected to remove the effects of the jacket flanges by normalizing the affected response curve to a reference response curve obtained away from the jacket flanges. As shown in FIG. 7, an effect of the jacket flanges on the response curve is a generally parallel shift in a downward direction in the intermediate and late time ranges (later than about 4 ms). That is to say that in the intermediate and late time ranges, the affected response curve is generally parallel to the reference response curves. The affected response curve is corrected by normalizing the affected response curve to the reference response curve in the intermediate time range.

FIG. 7 also serves to illustrate the effect that variations in distance between the antenna means and the pipe wall at one location on the pipe and between the antenna means and the pipe wall at another location on the pipe can have on responses. Such variations in distance result from non-uniform thicknesses of the insulation between the pipe wall and the jacket. Increasing the distance of the antenna means from the pipe wall causes the magnitude of the response to decrease at intermediate and late times, which decrease in magnitude shows up as a generally parallel shift. The responses can be corrected to remove the effects of variations in distance by normalizing the response curves to a reference response curve obtained with the antenna means at some known distance, in the intermediate time range.

The antenna means 27 gives a reading of the average conductor wall thickness over a search area. The size of the search area depends upon antenna size, antenna configuration and the duration of the receiver measuring time after each transmitter pulse. The search area of the antenna means increases with larger antenna sizes or with longer measuring times. In the preferred embodiment, the antenna means 27 has a diameter of about 3 inches. For a 10.5 inch pipe, the search area is about 12 inches in diameter.

Figure 8A:
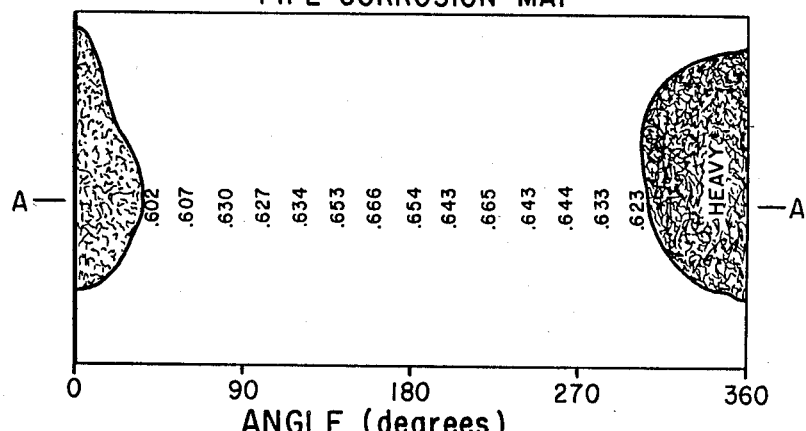
FIG. 8a is a circumferential map of a portion of a pipe showing both the location of corrosion and ultrasonic wall thickness measurements.

In the usual case, the portion of the pipeline that is to be investigated for corrosion is much larger than the search area of the antenna means. Therefore, a typical pipe survey requires the antenna means to be moved to new locations to complete the survey. In FIGS. 8a and through 8d there are shown a corrosion map of a pipe section and corresponding TEMP surveys or profiles along line A—A of the pipe section. In obtaining the TEMP profiles of FIGS. 8b through 8d, the antenna means was positioned at various locations along line A—A. In FIG. 8a, the numbers along line 8a indicate ultrasonic point measurements of the wall thickness (in inches) and the shaded areas indicate heavy corrosion, wherein the thickness of the pipe wall is less than for the unshaded areas. The map shows that the pipe wall along line A—A is thickest around 180° and gets thinner moving towards 0° and 360°.

Figure 8B:
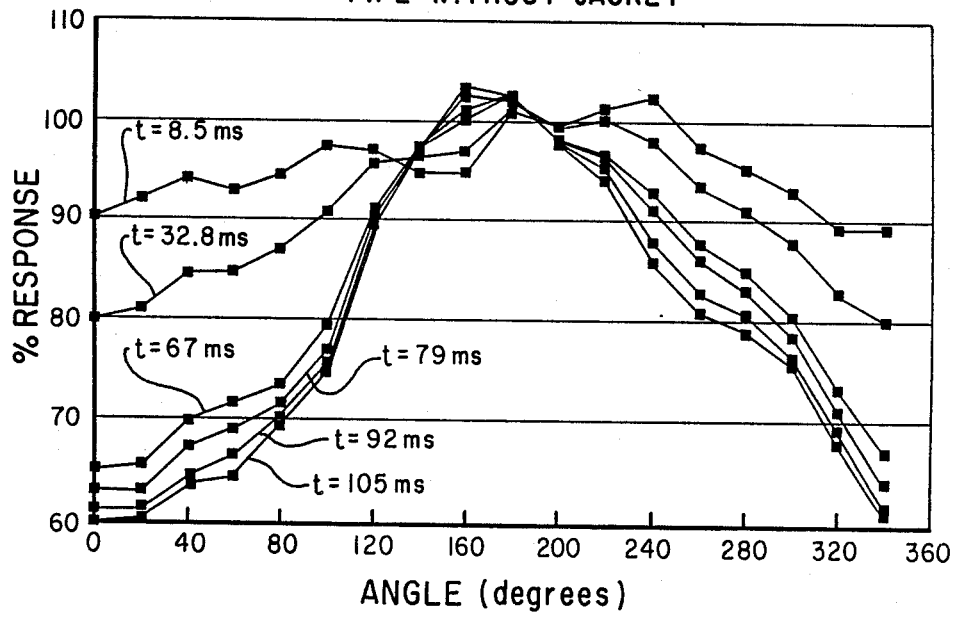
FIG. 8b is a graph showing transverse TEMP profiles of the unjacketed pipe of FIG. 8a, taken along line A—A.

FIG. 8b shows TEMP profiles of the pipe of FIG. 8a along line A—A, without a metal jacket. In FIG. 8b only those values of the response curve at selected discrete instances of time for each antenna means location are plotted. The response curve values at equivalent instances of time are then connected together to form a TEMP profile. Thus, for each antenna means location, the response curve values at time=8.5 ms, 32.8 ms, 67 ms, 79 ms, 92 ms, and 105 ms are plotted, forming respective TEMP profiles of pipe wall thickness. Each TEMP profile is normalized to the TEMP response obtained over the thickest portion of the pipe. As can be seen in FIG. 8b, the TEMP profiles show that in moving away from 180° in either direction (towards 0° and towards 360°) the pipe wall thickness lessens and is thinnest around 0° to 60° and 320° to 360°. The late time TEMP profiles (67 ms and greater) in particular clearly show the reduced wall thickness, corresponding with the pipe corrosion map of FIG. 8a.

Figure 8C:
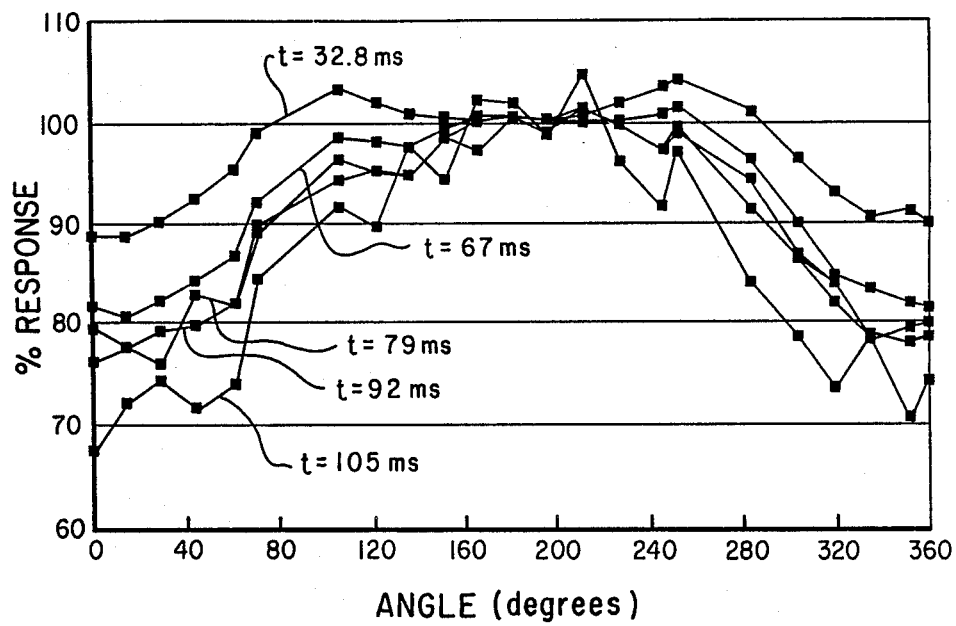
FIG. 8c is a graph showing transverse TEMP profiles of the jacketed pipe of FIG. 8a, taken along line A—A, with the TEMP profiles corrected for the effects of the jacket flanges.

In FIG. 8c, there are shown TEMP profiles of the pipe of FIG. 8a along line A—A, but with a metal jacket. The TEMP profiles of FIG. 8c were obtained in the same manner as the TEMP profiles of FIG. 8b. The jacket flanges, which are located at approximately 95° and 270°, have caused reductions in the amplitudes of the TEMP profile portions near the flanges. The TEMP profiles of FIG. 8c have been corrected to reduce the efforts of the jacket flanges by normalizing the responses measured near the jacket flanges to a response measured away from the jacket flanges. The responses are normalized in the intermediate time range (3-6 ms) and the late times (32 ms and greater) are then analyzed. (In FIG. 8d there are shown the TEMP profiles of FIG. 8c before the profiles have been corrected for the effects of the jacket flanges.) There is a good correlation between the TEMP profiles of FIG. 8c and the corrosion map of FIG. 8a. The TEMP profiles of FIG. 8c show that the pipe wall is reduced in thickness around 0° to 60° and 320° and 360°, thus leading to an inference of corrosion at those locations.

FIGS. 8a through 8d illustrate an advantageous difference of the TEMP method over the ultrasonic method. The ultrasonic method makes point measurements, requiring a large number of measurements, whereas the antenna means of the TEMP method has a large search area requiring fewer measurements. While the ultrasonic measurements in FIG. 8a are essentially confined to line A—A, the TEMP measurements encompass portions of the pipe extending for a few inches to either side of line A—A. Furthermore, ultrasonic measurements must be made on the bare pipe, while TEMP measurements can be made on the jacket.

Figure 8D:
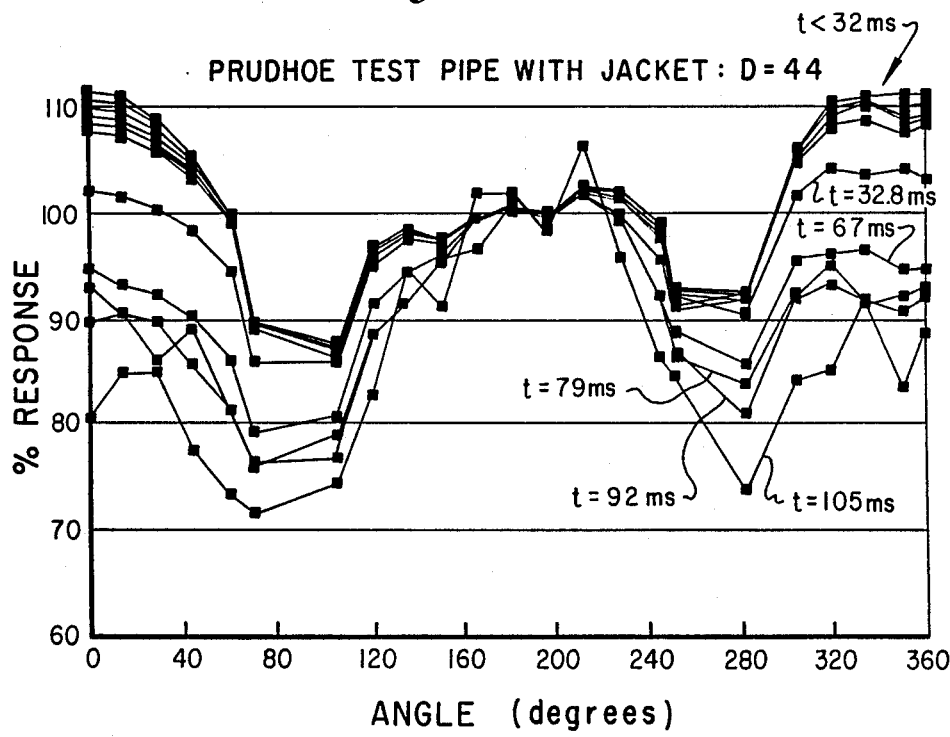
FIG. 8d is graph showing the same TEMP profiles as in FIG. 8c, but uncorrected for the effects of the jacket flanges.

For TEMP profiles such as are shown in FIGS. 8b-8d, the effects on the responses due to the variations in distance between the antenna means and the pipe wall, which variations are caused by moving the antenna means from one location on the pipe to another location, can be corrected for by creating reference response curves with the antenna means placed at a number of known distances from the pipe wall. The intermediate times of the response curves having distance error are then normalized to the intermediate times of the respective reference response curves.

Figure 6:
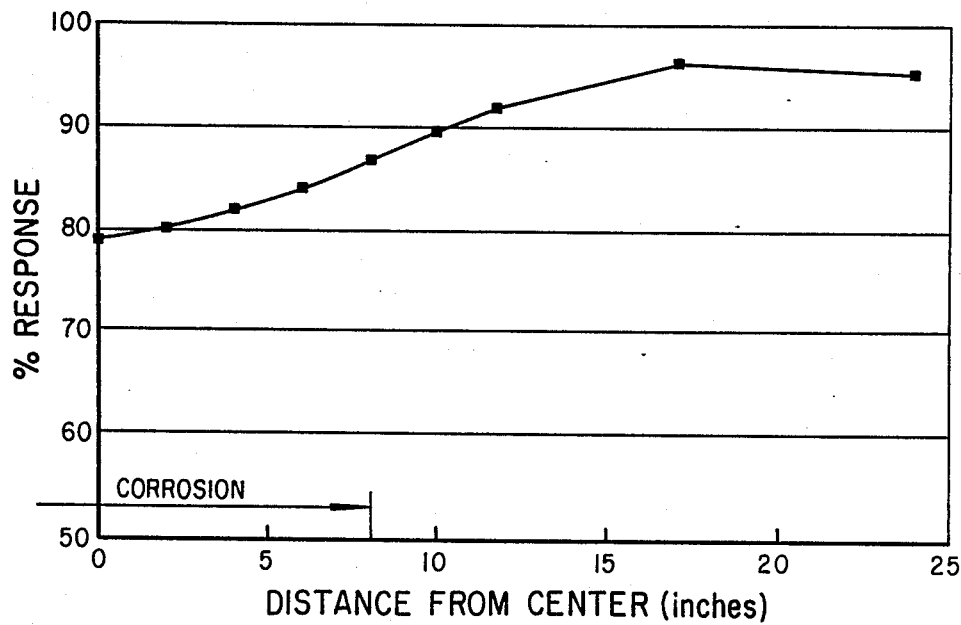
FIG. 6 is a graph showing a longitudinal cross-sectional TEMP profile of the pit of FIG. 5, with the profile being obtained by averaging the late time responses at each antenna means location.

In FIG. 6, there is shown a TEMP profile of the corrosion pit of FIG. 5. The TEMP profile is obtained by moving the antenna means to a plurality of locations and averaging the responses for the 25 to 52 ms time window at each antenna means location. The physical extent of the corrosion pit is indicated at the bottom left corner of the graph, which shows the pit to have a radius of about 8 inches. The TEMP profile of FIG. 6 shows a good correlation to the physical profile. From about 17 inches on, the TEMP profile shows a slight decrease in magnitude due to the induced currents interacting with the nearby pipe end.

Another method of interpretation of the response curves of FIG. 4 involves examining the time at which the far surface 47 of the pipe wall is initially manifested in the response curve. This time is referred to as the "critical time", and is that point where the response curve begins to break into a more pronounced downward direction than before, as discussed hereinbefore (see FIG. 4). The wall thickness of the pipe is proportional to the square root of the critical time. The constant or factor of proportionality is dependent on the geometry and the conductivity of the pipe, and may be determined by making a determination of the critical time of a particular thickness of the pipe.

The method of the present invention can be used to make quantitative measurements of wall thickness, once the instruments and data have been calibrated on pipes of known thickness and conductivity. Once the actual wall thickness of the investigated pipe is known, comparison to the manufactured wall thickness leads to a determination of wall loss due to corrosion on the investigated pipe.

An important aspect of the present invention is the increased accuracy of detection of corrosion on conductive walls over prior art methods. The present invention operates in the time domain rather than in the frequency domain. In the time domain, all the information needed to probe a conductor wall for accurate detection is obtained with one transmitter pulse. Each pulse contains an infinite number of frequencies. With frequency domain methods however, only a few frequencies are used to probe a conductor wall, resulting in a limited amount of information from which wall thickness is to be determined.

Another important aspect of the present invention is the ability to detect corrosion through insulation. Unlike ultrasonic methods, the present invention does not require the expensive and time consuming task of removing nonconductive and even conductive layers that are positioned between the wall of interest and the probe (the antenna means). Furthermore, the present invention has a greatly expanded research area associated with the antenna means, whereas the ultrasonic method produces essentially point measurements. This difference in probe search areas is of particular importance in detecting corrosion in pipeline walls. Corrosion in pipeline walls becomes hazardous when there is wall loss over a relatively large area. Small spots of corrosion, while generally a nuisance for potential leakages, do not present the explosive hazard that a large corroded area presents. The TEMP method is more efficient in detecting hazardous pipeline wall loss by giving an average measurement over the antenna means search area.

Although the method of the present invention has been described for use in detecting corrosion on pipelines, the method may also be used to detect corrosion on the electrically conductive walls of other types of container means such as storage vessels and pressure vessels. In addition, the method of the present invention can be used on uninsulated as well as insulated container means.

The antenna means can have the transmitting antenna and receiving antenna configured in arrangements other than the coincident arrangement described herein. One such arrangement has the transmitting antenna separate but coplanar with the receiving antenna. Another arrangement has a plurality of receiving antennas located within a large transmitting antenna loop.

Although this invention has been described with a certain degree of particularlity, it is understood that the present disclosure is made only by way of example and that numerous changes in the details of construction and the combination and arrangement of parts may be resorted to without departing from the spirit and the scope of the invention, reference being had for the latter purpose to the appended claims.

What is claimed is:

1. A method of detecting corrosion on walls of container means, said walls being electrically conductive and having near surfaces and far surfaces, comprising the steps of:
   a. placing transmitting antenna means and receiving antenna means in proximity with the near surface of that portion of the container means wall which is to be investigated for corrosion;
   b. energizing the transmitting antenna means with current;
   c. abruptly de-energizing the transmitting antenna means so as to induce current into the container means wall portion;
   d. detecting the presence of and the decay of said induced current in said container means wall portion with the receiving antenna means;
   e. creating a record of the decay with said induced current in said container means wall portion over a period of time;
   f. examining said record to determine the decay of said induced current and comparing the decay of the induced current to the decays of induced current of reference records, said reference records being obtained from reference container means with known wall thicknesses, wherein the presence or absence of corrosion on the container means wall portion can be inferred from said indicated thickness.

2. The method of claim 1 wherein said transmitting antenna means and said receiving antenna means are placed adjacent a layer of insulation that is adjacent said container means wall such that the insulation is interposed between said container means wall and said transmitting antenna means and said receiving antenna means, wherein said method of detecting corrosion can be performed with said insulation remaining intact on said container means.

3. The method of claim 2 wherein said transmitting antenna means and said receiving antenna means are placed adjacent a conductive jacket that is adjacent said container means wall such that said jacket is interposed between said container means wall and said transmitting antenna means and said receiving antenna means, said jacket having a wall thickness substantially less than the wall thickness of said container means, wherein said method of detecting corrosion can be performed with said jacket remaining intact on said container means.

4. The method of claim 1 wherein said record from said investigated container means wall portion and said reference records have respective portions where the rate of decay changes from a relatively constant rate of decay to an accelerating rate of decay, further comprising the step of interpreting said record for an indication of the thickness of said investigated container means wall portion, so that the presence or absence of corrosion on the container means wall portion can be inferred, by comparing the accelerating rate of decay portion of said record to the accelerating rate of decay portions of said reference records, wherein if the accelerating rate of decay portion of said record decays faster than the accelerating rate of decay portions of said reference records then the wall thickness of said investigated container means wall portion is thinner than the wall thickness of said reference records.

5. The method of claim 2 wherein said record from said investigated container means wall portion and said reference records have respective portions where the rate of decay changes from a relatively constant rate of decay to an accelerating rate of decay, further comprising the step of interpreting said record for an indication of the thickness of said investigated container means wall portion, so that the presence or absence of corrosion on the container means wall portion can be inferred, by comparing the acceleration rate of decay portion of said record to the accelerating rate of decay portions of said reference records, wherein if the accelerating rate of decay portion of said record decays faster than the accelerating rate of decay portions of said reference records then the wall thickness of said investigated container means wall portion is thinner than the wall thickness of said reference records.

6. The method of claim 3 wherein said record from said investigated container means wall portion and said reference records have respective portions where the rate of decay changes from a relatively constant rate of decay to an accelerating rate of decay, further comprising the step of interpreting said record for an indication of the thickness of said investigated container means wall portion, so that the presence or absence of corrosion on the container means wall portion can be inferred, by comparing the accelerating rate of decay portion of said record to the accelerating rate of decay portions of said reference records, wherein if the accelerating rate of decay portion of said record decays faster than the accelerating rate of decay portions of said reference records then the wall thickness of said investigated container means wall portion is thinner than the wall thickness of said reference records.

7. The method of claim 6 wherein said jacket is provided in portions, with said jacket portions having seam means for joining said jacket portions together, with said seam means having an effect on the decay of said induced current in said container means wall portion, further comprising the step of:
   a. correcting the record of the decay of said induced current in said container means wall portion for the effects of said seam means by normalizing said record to said reference record over those portions of the record where said records are generally parallel, said reference record being created as a record of the decay of a similarly induced current in a portion of a substantially similar container means wall that is located some distance away from seam means such that said reference record is unaffected by seam means.

8. The method of claim 5 wherein said insulation has a non-uniform thickness causing variations in the distance between the transmitting antenna means and the receiving antenna means and the container means wall at said investigated portion and between the transmitting antenna means and the receiving antenna means and the container means wall at a second investigated portion with said variations in distance having an effect on the decay of said induced current in said container means wall portion, further comprising the step of:
   a. correcting the record of the decay of said induced current in said container means wall portion for the effects of said variations in distance by normalizing said record to said reference record over those portions of the records where said records are generally parallel, said reference record being created with said transmitting antenna means and said receiving antenna means located at known distances from said conductor means wall portion.

9. The method of claim 6 wherein said insulation has a non-uniform thickness causing variations in the distance between the transmitting antenna means and the receiving antenna means and the container means wall at said investigated portion and between the transmitting antenna means and the receiving antenna means and the container means wall at a second investigated portion with said variations in distance having an effect on the decay of said induced current in said container means wall portion, further comprising the step of:

a. correcting the record of the decay of said induced current in said container means wall portion for the effects of said variations in distance by normalizing said record to a reference record over those portions of the records where said records are generally parallel, said reference record being created as a record of the decay of a similarly induced current in a portion of a substantially similar container means wall with said transmitting antenna means and said receiving antenna means located at known distances from said conductor means wall portion.

10. The method of claim 1 further comprising the step of determining the time in said record that said induced current reaches the far surface of the investigated container means wall portion, wherein the thickness of said investigated container means wall portion is indicated.

11. The method of claim 1, further comprising the steps of:

a. keeping the transmitting and receiving antenna means in the same location and creating a plurality of records of the decay of similarly induced currents for that transmitting and receiving antenna means location, b. processing said plurality of records to increase the signal-to-noise ratio for the transmitting and receiving antenna means location.

12. A method of measuring wall thickness to detect irregularities such as corrosion on electrically conductive walls of container means, comprising the steps of:

a. providing transmitting antenna means, receiving antenna means, transmitter means connected with said transmitting antenna means, and receiver means connected with said receiving antenna means;

b. placing said transmitting antenna means and said receiving antenna means in proximity to that portion of the container means wall which is to be investigated for irregularities;

c. providing an abruptly changing current to said transmitting antenna means from said transmitter means so as to induce current into the investigated container means wall portion;

d. detecting said induced current in said investigated container means wall portion with said receiving antenna means and said receiver means to produce a first received signal, said first received signal decaying into noise over a period of time, said first received signal having intermediate and late time ranges;

e. examining said first received signal intermediate and late time ranges to determine the decay of said first received signal, and comparing the decay of said first received signal to the decay of said second received signal obtained from another container means wall portion which is free of irregularities, wherein said first received signal decay from said investigated container means wall portion gives an indication of the thickness of the investigated container means wall portion and the presence or absence of irregularities on the investigated container means wall portion can be determined.

13. The method of claim 12 wherein each of said first and second received signals has a portion in said intermediated or late time ranges where the rate of decay changes from a relatively constant rate of decay to an accelerating rate of decay, further comprising the step of comparing the accelerating rate of decay portion of the first received signal to the accelerating rate of decay portion of the second received signal, wherein if the accelerating rate of decay portion of said first received signal decays faster than the accelerating rate of decay portion of said second received signal then the wall thickness of said investigated container wall means wall portion is thinner than the wall thickness of said other container means wall portion.

14. The method of claim 13 wherein said container means wall is provided with a layer of insulation, said insulation being located adjacent to said container means wall so as to be interposed between said container means wall portion and said transmitting antenna means and said receiving antenna means, wherein said transmitting antenna means induces current into the investigated container means wall portion through said insulation and said receiving antenna means detects said induced current through said insulation.

15. The method of claim 14 wherein said insulation has a non-uniform thickness causing variations in the distance between the transmitting antenna means and the receiving antenna means and the container means wall at said investigated portion and between the transmitting antenna means and the receiving antenna means and the container means wall at a second investigated portion with said variations in distance having an effect on the decay of said induced current in said container means wall portion, further comprising the step of:

a. correcting the first received signal for the effects of said variations in distance by normalizing the first received signal to a reference signal over the intermediate time ranges of said signals, said reference signal being created with the transmitting antenna means and the receiving antenna means located at known distances from the container means wall portion.

16. The method of claim 13 wherein said container means wall is provided with a layer of insulation and a conductive jacket, said insulation and said jacket being located adjacent to said container means wall such that said insulation is interposed between said container means wall and said jacket, said jacket being interposed between said insulation and said transmitting antenna means and said receiving antenna means, wherein said transmitting antenna means induces current into the container means wall portion through said insulation and said jacket and said receiving antenna means detects said induced current through said insulation and said jacket.

17. The method of claim 16 wherein said jacket is provided in portions, with said jacket portions having seam means for joining said jacket portions together, with said seam means having an effect on the decay of said induced current in said container means wall portion, further comprising the step of:

a. correcting the first received signal for the effects of said seam means by normalizing the first received signal to a reference signal over the intermediate time ranges of said signals, said reference signal being created with the transmitting antenna means and the receiving antenna means located some distance away from a seam means on a container means such that the reference signal is unaffected by said seam means.

18. A method of measuring wall thickness to detect irregularities such as corrosion on electrically conductive walls on container means, comprising the steps of:
  a. providing transmitting antenna means, receiving antenna means, transmitter means connected with said transmitting antenna means, and receiver means connected with said receiving antenna means;
  b. placing said transmitting antenna means and said receiving antenna means in proximity to that portion of the container means wall which is to be investigated for irregularities;
  c. providing an abruptly changing current to said transmitting antenna means from said transmitter means so as to induce current into the investigated container means wall portion;
  d. detecting said induced current in said investigated container means wall portion with said receiving antenna means and said receiver means to produce a first received signal, said first received signal decaying into noise over a period of time, said first received signal having intermediate and late time ranges;
  e. examining said first received signal intermediate and late time ranges to determine the decay of said first received signal;
  f. repeating the above steps so as to obtain other received signals from other portions of the container means wall;
  g. comparing the decay of said first received signal to the decays of said other received signals obtained from said other portions of the container means wall, wherein said first received signal gives an indication of the thickness of the investigated container means wall portion relative to the other portions of the container means wall in the presence or absence of irregularities on the investigated container means wall portion can be determined.

19. The method of claim 18 wherein each of said received signals has a portion where the rate of decay changes from a relatively constant rate of decay to an accelerating rate of decay, further comprising the step of comparing the accelerating rate of decay portion of the first received signal to the accelerating rate of decay portions of the other received signals, wherein if the accelerated rate of decay portion of said first received signal decay faster than the accelerating rate of decay portions of said other received signals then the wall thickness of said investigated container means wall portion is thinner than the wall thickness of said other container means wall portions.

20. The method of claim 19 wherein said transmitting antenna means and said receiving antenna means comprising a coincident antenna arrangement.

21. A method of measuring wall thickness to detect irregularities such as corrosion on electrically conductive walls of container means, comprising the steps of:
  a. providing transmitting antenna means, receiving antenna means, transmitter means connected with said transmitting antenna means, and receiver means connected with said receiving antenna means;
  b. placing said transmitting antenna means and said receiving antenna means in proximity to that portion of the container means wall which is to be investigated for irregularities;
  c. providing an abruptly changing current to said transmitting antenna means from said transmitter means so as to induce current into the investigated container means wall portion;
  d. detecting said induced current in said investigated container means wall portion with said receiving antenna means and said receiver means to produce a first received signal, said first received signal decaying into noise over a period of time, said first received signal having intermediate and late time ranges;
  e. examining said first received signal intermediate and late time ranges to determine the decay of said first received signal, and comparing the decay of said first received signal to the decay of a reference signal to determine the wall thickness of said investigated container means wall portion, said reference signal being obtained from a reference container means with a known wall thickness, wherein the presence or absence of irregularities on the investigated container means wall portion can be determined.

22. The method of claim 21 wherein each of said first and reference received signals has a portion where the rate of decay changes from a relatively constant rate of decay to an accelerating rate of decay, further comprising the step of comparing the accelerating rate of decay portion of the first received signal to the accelerating rate of decay portion of the reference received signal, wherein if the accelerated rate of decay portion of said first received signal decays faster than the accelerated rate of decay portion of said reference received signal then the wall thickness of said investigated container wall means wall portion is thinner than the wall thickness of said reference container means wall portion.

23. The method of claim 22 wherein said container means wall is provided with a layer of insulation, said insulation being located adjacent to said container means wall so as to be interposed between said container means wall portion and said transmitting antenna means and said receiving antenna means, wherein said transmitting antenna means induces current into the investigated container means wall portion through said insulation and said receiving antenna means detects said induced current through said insulation.

24. The method of claim 23 wherein said insulation has a non-uniform thickness causing variations in the distance between the transmitting antenna means and the receiving antenna means and the container means wall at said investigated portion and between the transmitting antenna means and the receiving antenna means and the container means wall at a second investigated portion with said variations in distance having an effect on the decay of said induced current in said container means wall portion, further comprising the step of:
  a. correcting the first received signal for the effects of said variations in distance by normalizing the first received signal to said reference signal over the intermediate time ranges of said signals, said reference signal being created with the transmitting antenna means and the receiving antenna means located at known distances from the container means wall portion.

25. The method of claim 22 wherein said container means wall is provided with a layer of insulation and a conductive jacket, said insulation and said jacket being located adjacent to said container means wall such that said insulation is interposed between said container means wall and said jacket, said jacket being interposed between said insulation and said transmitting antenna means and said receiving antenna means, wherein said transmitting antenna means induces current into the container means wall portion through said insulation and said jacket and said receiving antenna means detects said induced current through said insulation and said jacket.

26. The method of claim 25 wherein said jacket is provided in portions, with said jacket portions having seam means for joining said jacket portions together, with said seam means having an effect on the decay of said induced current in said container means wall portion, further comprising the step of:
   a. correcting the first received signal for the effects of said seam means by normalizing the first received signal to said reference signal over the intermediate time ranges of said signals, said reference signal being created with the transmitting antenna means and the receiving antenna means located some distance away from a seam means on a container means such that the reference signal is unaffected by said seam means.

27. A method of measuring wall thickness to detect irregularities such as corrosion on electrically conductive walls of container means, comprising the steps of:
   a. providing transmitting antenna means, receiving antenna means, transmitter means connected with said transmitting antenna means, and receiver means connected with said receiving antenna means;
   b. placing said transmitting antenna means and said receiving antenna means in proximity to that portion of the container means wall which is to be investigated for irregularities;
   c. providing an abruptly changing current to said transmitting antenna means from said transmitter means so as to induce current into the investigated container means wall portion;
   d. detecting said induced current in said investigated container means wall portion with said receiving antenna means and said receiver means to produce a received signal, said received signal decaying into noise over a period of time, said received signal having intermediate and late time ranges, said received signal having a critical time which is the time when the rate of decay of said received signal changes from a relatively constant rate of decay to an accelerating rate of decay;
   e. examining said received signal to determine the critical time of said received signal;
   f. determining a factor of proportionality between the wall thickness of said investigated container means wall portion and the critical time by examining the critical times of reference received signals, said reference received signals obtained from a reference container means having known wall thicknesses;
   g. determining the thickness of said investigated container means wall portion by applying said factor of proportionality to the square root of the critical time.

28. The method of claim 27 wherein said container means wall is provided with a layer of insulation, said insulation being located adjacent to said container means wall so as to be interposed between said container means wall portion and said transmitting antenna means and said receiving antenna means, wherein said transmitting antenna means induces current into the investigated container means wall portion through said insulation and said receiving antenna means detects said induced current through said insulation.

29. The method of claim 28 wherein said insulation has a non-uniform thickness causing variations in the distance between the transmitting antenna means and the receiving antenna means and the container means wall at said investigated portion and between the transmitting antenna means and the receiving antenna means and the container means wall at a second investigated portion with said variations in distance having an effect on the decay of said induced current in said container means wall portion, further comprising the step of:
   a. correcting the received signal for the effects of said variations in distance by normalizing the received signal to a second received signal over the intermediate time ranges of said signals, said second received signal being created with the transmitting antenna means and the receiving antenna means located at known distances from the container means wall portion.

* * * * *

UNITED STATES PATENT AND TRADEMARK OFFICE
CERTIFICATE OF CORRECTION

PATENT NO. : 4,843,320
DATED : June 27, 1989
INVENTOR(S) : Brian R. Spies

It is certified that error appears in the above—identified patent and that said Letters Patent is hereby corrected as shown below:

In the Claims,

> in claim 5, column 10, line 7, change "acceleration" to --accelerating--.
>
> In claim 13, column 12, lines 5-6, change "intermediated" to --intermediate--.

Signed and Sealed this

Nineteenth Day of February, 1991

Attest:

HARRY F. MANBECK, JR.

*Attesting Officer*    *Commissioner of Patents and Trademarks*